United States Patent [19]

Speiser et al.

[11] Patent Number: 4,851,439

[45] Date of Patent: Jul. 25, 1989

[54] FUMARIC ACID DERIVATIVES, PROCESS FOR THE PRODUCTION THEREOF AND PHARMACEUTICAL COMPOSITIONS CONTAINING SAME

[76] Inventors: Peter P. Speiser, Freudenbergstr. 101/D2, 8044 Zürich; Rajendra K. Joshi, Badenerstr. 795, 8048 Zürich, both of Switzerland

[21] Appl. No.: 814,668

[22] Filed: Dec. 30, 1985

[30] Foreign Application Priority Data

Jan. 15, 1985 [CH] Switzerland .................. 161/85

[51] Int. Cl.$^4$ ................ A61K 31/225; A61K 7/40; A01N 37/02; C07C 55/00
[52] U.S. Cl. ................ 514/547; 514/574; 514/863; 562/512.4; 562/590; 562/595
[58] Field of Search ............ 536/119; 562/595, 512.4, 562/582, 590, 596; 514/529, 557, 723, 784, 785, 863, 547, 574

[56] References Cited

U.S. PATENT DOCUMENTS

| 2,218,181 | 10/1940 | Searle et al. | 514/547 |
| 3,773,946 | 11/1973 | Creger | 514/547 |
| 4,346,118 | 8/1982 | Islam | 514/547 |
| 4,677,119 | 6/1987 | Dymicky et al. | 514/547 |

FOREIGN PATENT DOCUMENTS

| 2530372 | 1/1977 | Fed. Rep. of Germany | 514/547 |
| 45-20118 | 7/1970 | Japan | 514/547 |
| 0649551 | 1/1951 | United Kingdom | 562/595 |

OTHER PUBLICATIONS

Safrin, L. et al., Chemical Abstracts, vol. 96: 183226c (1982).
Hoelzer, A. et al., Chemical Abstracts, vol. 96: 40799f (1982).
Zecher, W. et al., Chemical Abstracts, vol. 98: 197614f (1983).

*Primary Examiner*—Ronald W. Griffin
*Assistant Examiner*—Nancy S. Carson
*Attorney, Agent, or Firm*—Cohen, Pontani & Lieberman

[57] ABSTRACT

Fumaric acid derivatives of the formula

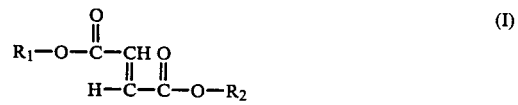

wherein
$R_1$ is a hydrogen atom, a $C_1$-$C_8$ alkyl group or a metallic cation, and
$R_2$ is a saturated or unsaturated aliphatic $C_6$-$C_{24}$ alkyl group, psoralen-9-yl, retinyl, α-tocopheryl (vitamin E), calciferyl, corticosteroid-21-yl or monosaccharid-ω-yl; a group of fumaric acid derivatives based on glycerol, alkane diol or polyol molecules; and fumaric acid derivatives of the forumla

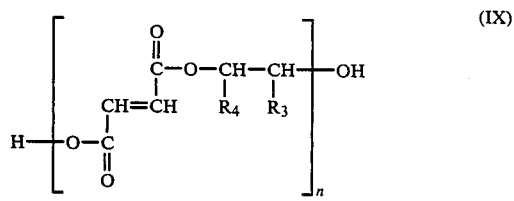

wherein
n is an interger from 30 to 260,
$R_3$ is a hydrogen atom or a $C_1$-$C_3$ alkyl group,
$R_4$ is one of the $R_3$ groups and n is the number of molecule repetitions, processes for their production and compositions containing same are described. These compounds are useful as drugs for the treatment of cryptogenically-caused diseases and have antisporiatic as well as antimicrobial action.

9 Claims, No Drawings

FUMARIC ACID DERIVATIVES, PROCESS FOR THE PRODUCTION THEREOF AND PHARMACEUTICAL COMPOSITIONS CONTAINING SAME

FIELD OF THE INVENTION

The present invention relates to new fumaric acid derivatives, methods for their preparation and pharmaceutical compositions containing them which contain fumaric acid in the form of pro-drugs as active principle.

BACKGROUND ART

Pharmaceutical preparations which, after administration, enter into the citric acid cycle upon their biological degradation or belong thereto are gaining greater and greater importance in therapy, generally in high dose, since it is possible by the use thereof to mitigate or cure cryptogenically caused diseases. Thus, fumaric acid impedes the growth of the Ehrlich ascitic tumor in mice, reduces the toxic effects of mitromycin C and aflatoxin (Kuroda, K. M. Akao, Biochem. Pharmacol. 29, 2839–2844, 1980/Gann. 72, 777–782, 1981/Cancer Res. 36. 1900–1903, 1976) and possesses an antipsoriatic as well as antimicrobial action (C. N. Huhtsnen, J. Food Sci., 48, 1574 (1983), M. N. Islam, U.S. Pat. No. 4,346,118 of Aug. 24, 1982/C.A., 97, 161317b (1982)).

High doses of administration of fumaric acid, its salts or its previously known derivatives such as dihydroxy fumaric acid, fumaramide and fumaronitrile have, upon parenteral, dermal and particularly peroral administration such an unacceptable rate of side effects and high toxicity (P. Holland, R. G. White, Brit. J. Dermatol. 85, 259–263, 1971), that it has heretofore been necessary generally to refrain from such therapy.

SUMMARY OF THE INVENTION

The new fumaric acid derivatives of the invention and pharmaceutical compositions which contain them contain amphiphilic full or semiesters of fumaric acid. In this connection, on the one hand, the one carboxyl group of the fumaric acid can be esterified with a lipid, generally long-chain aliphatic alcohols such as, for instance, a fatty alcohol of a medium-chain length of between 6 and 24 carbon atoms, and the other carboxyl group of the fumaric acid can be present in free form or be esterified with lower aliphatic alcohols having 1 to 8 carbon atoms. The fumaric acid can also be found as monomethyl or ethyl ester to a mono- or diglyceride, glycerol or polyol molecule. These pro-drugs, which are not therapeutically effective as such and become so only during or after resorption or after their systemic incorporation in the body by ubiquitously present enzyme sytems (esterases and lipases, etc.), are converted to the biologically active fumarate anion.

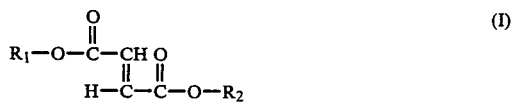

The previously known salts and derivatives of fumaric acid were not resorbed, or only insufficiently resorbed, due to their relatively strongly polar hydrophilic character, during their short residence time on lipophilic organ boundary layers. For this reason, high doses must be used, which gave rise to many side effects (eructation, dizziness, nausea, vomiting, abdominal and intestinal cramps, flush syndrome).

The fumaric acid derivatives of the invention represent amphiphilic (ambiphilic) pro-drugs which have boundary surface active properties, are readily resorbable and distributable, are converted within the body in controlled manner into the active fumarate anion, and surprisingly do not exhibit the previously known side effects. The compounds of the invention are substantially better tolerated, no longer have the above-mentioned side effects and are resorbed better in view of their lipophilic to amphiphilic character. With the new pro-drug systems of the invention the entire molecule is simultaneously imparted lipophilic and hydrophilic properties, as a result of which better membrane or boundary-layer passage is made possible. Through variation of the substituents, the amphiphilic property (hydrophile-lipophile balance, distribution coefficient) of the entire molecule can be better adjusted to an optimal membrane passage of the target organ aimed at in each case.

The use in accordance with the invention of nonpolar and weakly polar substituents assures not only optimum resorption and distribution but also controlled and controllable liberation of the fumarate anion by ester hydrolysis by means of enzyme systems inherent in the body without fragmentary molecules or metabolites which have physiologically undesired properties occurring upon their degradation.

With the fumaric acid derivatives of the invention, the fumaric acid is bound entirely or partially to lipids (fatty alcohols, phosphatides, glycerol, mono- and diglycerides). By selection of the lipid portion the lipophilia to amphiphila of the entire molecule can be controlled. Examples of suitable lipids are ones which have a saturated or unsaturated aliphatic chain of between 6 and 24 carbon atoms, such as, for example, valeryl alcohol, capryl alcohol, lauryl alcohol, palmityl alcohol, stearyl alcohol, cetyl alcohol, oleyl alcohol, linoleyl alcohol, ricinoyl alcohol, melissyl alcohol, cerotyl alcohol as well as phosphatidyl alcohol, lysolecithin, etc.

The present invention relates to fumaric acid derivatives of general formula (I)

$$R_1-O-\overset{\overset{O}{\|}}{C}-\overset{\|}{\underset{H-C-C-O-R_2}{CH}}\overset{O}{\underset{\|}{}} \quad (I)$$

in which
$R_1$ is a hydrogen atom, a $C_1$–$C_8$ alkyl group or a metallic cation such as, for example, Na, Ca or Zn, and
$R_2$ is a saturated or unsaturated aliphatic $C_6$–$C_{24}$ alkyl group, psoralen-9-yl, retinyl, α-tocopheryl (vitamin E), calciferyl, corticosteroid-21-yl or monosaccharid-ω-yl (for instance, glucose-6-yl), and also to fumaric acid derivatives of general formula (II), (III), (IV), (V), based on a glycerol or alkane diol or polyol molecule of the general formulas

-continued

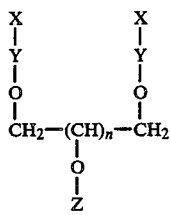
(III)

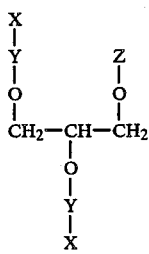
(IV)

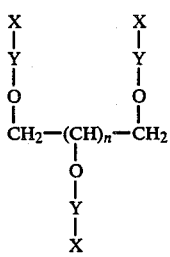
(V)

wherein
n is an integer from 1 to 3, Y is the fumaric ester group of formula (VI)

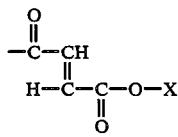
(VI)

X is a hydrogen atom, a $CH_3$ or $C_2H_5$ group or a metallic cation,

Z is a saturated or unsaturated $C_6$–$C_{24}$ acyl group of formula (VII)

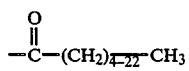
(VII)

a grouping of formula (VIII)

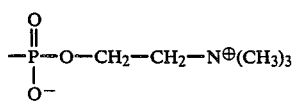
(VIII)

or a hydrogen atom, and OZ is a hydrogen atom or a $C_1$–$C_8$ alkyl group; and to fumaric acid derivatives of general formula (IX)

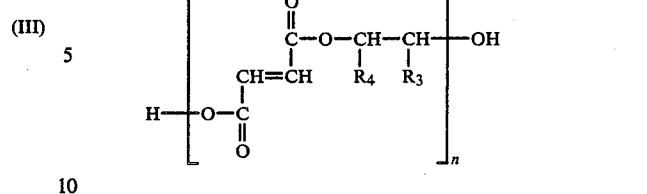
(IX)

in which
n is an integer from 30 to 260,
$R_3$ is a hydrogen atom or a $C_1$–$C_3$ alkyl group,
$R_4$ is one of the $R_3$ groups and n is the number of molecule repetitions.

The present invention also relates to a process for producing fumaric acid derivatives of formula (I), above, characterized in that a compound of general formula (X)

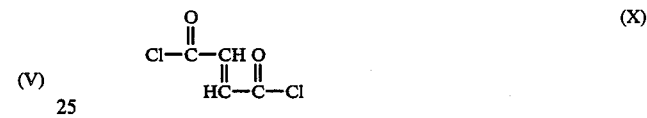
(X)

(a) is condensed with 2 moles of alkyl alcohol ($R_2OH$) to form the diester and then hydrolyzed in controlled manner to form the monoester, or (b) is condensed with 1 mole of a corresponding alkyl alcohol ($R_2OH$) and the resultant monoacid chloride is hydrolyzed to the acid, or (c) fumaric acid is condensed directly with two moles of an alkyl alcohol ($R_2OH$) in accordance with formula (I), above, to form a diester and then hydrolyzed in controlled manner to form the monoester, or (d) maleic acid or maleic anhydride is condensed directly with 1 to 2 moles of the corresponding alkyl alcohol ($R_2OH$) according to formula (I), above, to form a mono- or diester and then catalytically isomerized to form the corresponding fumaric acid derivative, $R_2$ having the meaning as above indicated.

The present invention relates further to a process for producing fumaric acid derivatives of formula (I), above, characterized in that a compound of general formula (XI)

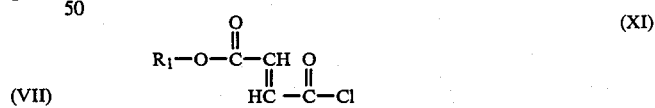
(XI)

in which $R_1$ has the meaning above indicated, is condensed with one mole of a corresponding alkyl alcohol ($R_2OH$), with the formation of an ester of the $R_2$ grouping according to formula (I) above; and to a process for producing fumaric acid compounds having the general formulas (II), (III), (IV) and (V), above, characterized in that a compound of general formula (XII)

(XII)

is reacted with a carboxylic acid chloride of general formula (XIII) or (XIV)

Z—Cl (XIII),

X—Y—Cl (XIV), in which Z, X and Y have the meanings indicated above, and the resultant carbonyl components are reduced to the corresponding hydroxy compounds and possibly reacted with carboxylic acid chloride of general formula (XIV) or (XIII).

The instant invention further relates to a process for producing fumaric acid derivatives of general formulas (II), (III), (IV) and (V), above, characterized in that glycerol, alkane diol or polyol is reacted with a carboxylic acid chloride of general formula (XIII) and (XIV), above, wherein X, Y and Z have the meanings indicated; and a process for producing fumaric acid derivatives of general formula IX, above, characterized in that one mole of fumaric acid is condensed with one mole of a compound of general formula (XV)

$$R_3-CH-CH-R_4 \atop OH \quad OH \qquad (XV)$$

to form a polyester, $R_3$ and $R_4$ having the meanings indicated above.

Objects of the present invention are further pharmaceutical compositions containing fumaric acid derivatives of general formula (I), above, for oral administration in the form of capsules, granulates and tablets, for cutaneous and transdermal administration in the form of ointments, plasters, lotions and douche agents, for parenteral administration in the form of aqueous microdispersions, O/W-emulsions or oily solutions, for rectal administration as suppositories or microenemas, and for the medicinal treatment of hair and of finger and toe nails; and pharmaceutical compositions containing fumaric acid derivatives of general formula (II) to (V) and (IX), above, for oral administration in the form of capsules, granulates and tablets, for cutaneous and transdermal administration in the form of ointments, plasters, lotions and douche agents, for parenteral administration in the form of aqueous microdispersions, O/W-emulsions or oily solutions, for rectal administration as suppositories or micorenemas, and for the medicinal treatment of hair and of finger and toe nails.

EXAMPLE 1

Preparation of cetylethylfumarate (Full Ester)

60.61 g (0.25 mole)/1-hexadecanol (MW 242.45) are dissolved in 300 ml of ethanol-free chloroform and 25 ml of absolute pyridine (0.31 mole) and by the dropwise addition of a solution of 44.7 g of fumaric acid monoethylesterchloride (0.275 mole, MW 162.45) in 100 ml of purified chloroform maintained at a constant 35° C. After completion of the reaction the violet reaction mixture is diluted with 800 ml of petroleum ether and purified by washing with 100 ml each of water, 2×1N hydrochloric acid, water, 5% $Na_2CO_3$ and water, dried and the solvent removed (rotary evaporator). The solid residue was recrystallized several times from petroleum ether or 94% ethanol, a total of 70 g of product, corresponding to 79% of the theoretical yield, being obtained ($C_{22}H_{40}O_4$, MW 368.56), MP 32° C.

Analysis: For the empirical formula: $C_{22}H_{40}O_4$; Calculated: C 71.7, H 10.9, O 17.4; Found: C 71.7, H 10.9, O 17.5.

EXAMPLE 2

Preparation of ethyl octadecyl fumarate (Full Ester)

135 g (0.5 mole) of 1-octadecanol and 65 ml (0.55 mole) of quinoline are dissolved, with stirring, at 40° C. in 500 ml of ethanol-free chloroform. Over the course of one hour, 89.4 g (0.55 mole) of fumaric acid monoethylesterchloride were added drop by drop to the clear solution and it was boiled for 2 hours under reflux. The reaction mixture was diluted with 500 ml of petroleum ether and extracted twice with 0.5N hydrochloric acid, water, 5% potassium carbonate solution and water, dried over sodium sulfate and concentrated under reduced pressure. The solid residue was recrystallized from 95% ethanol. Yield: 139 g of product having a melting point of 42° C.

Analysis: For the empirical formula: $C_{24}H_{44}O_4$; Calculated: C 72.7, H 11.2, O 16.1, Found: C 73.0, H 11.4, O 16.2.

EXAMPLE 3

Preparation of octyl-hydrogen fumarate (semi-ester)

A solution of 72.78 g of absolute pyridine (0.92 mole, MW 79.1), 119.81 g octanol (0.92 mole, MW 130.23) and 120 ml of ethanol-free chloroform is supercooled with 70.6 g of fumaric acid dichloride (0.46 mole, MW 152.97), converted at room temperature into the dioctyl ester, diluted to 750 ml with petroleum ether, and purified by washing with 0.1N HCl, water, 5% $Na_2CO_3$ solution and water, dried, filtered and the solvent removed on a rotary evaporator. The product was purified by distillation at 0.35 mmHg and 175° C. The hydrolysis of the monooctylester is effected under reflux in a potassium-hydroxide solution in 60% ethanol for 2 hours. After addition of water, purification is effected with petroleum ether, the aqueous phase is brought to a pH of 4 by means of dilute hydrochloric acid solution and extracted three times with chloroform. The combined chloroform extracts are dried, filtered, concentrated and recrystallized from petroleum ether (MP 67° C.). An 0.1% solution dissolved in Myglyol 810 showed by the ring method with respect to water an interfacial tension of 6.1 L $mN^{-1}$.

Analysis: For the empirical formula: $C_{12}H_{20}O_4$; Calculated: C 63.1, H 8.8, O 28.0, Found: C 62.9, H 8.8, O 28.1.

EXAMPLE 4

Preparation of dodecyl hydrogen fumarate (semi-ester)

122.3 g (0.8 mole) of fumaric acid dichloride in 100 ml of benzene p.a. were heated to 65° C. To the heated solution there were slowly added, drop by drop, over the course of three hours, 149 g (0.8 mole) of dodecanol dissolved in 300 ml benzene p.a., followed by stirring for a further 10 hours at 80° C. The solvent and the remaining fumaric acid dichloride were removed under reduced pressure. An acetone-water mixture was added to the residue for the acid chloride hydrolysis. The white precipitate was filtered off, thoroughly washed with water, dried, and recrystallized from petroleum ether or 80% ethanol.

Yield: 120 g of product having a melting point of 78.4° C.

EXAMPLE 5

Preparation of 1,3-dipalmitoyl-2-glycerol-ethfumarate

Starting with absolute dihydroxyacetone, conversion is effected in an anhydrous mixture of chloroform and pyridine with palmitic acid or capronic acid chloride to the corresponding 1,3-dihydroxypropan-2-one-1,3-dipalmitate or 1,3-dicapronate. Thereupon reduction is effected with sodium boron hydride ($NaBH_4$) in known manner to the corresponding propanol derivative, which is converted, in a mixture of absolute pyridine and ethanol-free chloroform with fumaric acid monoethylester chloride with cooling to the long-chain palmityl or short-chain capronic pro-drug, in which connection a temperature of 27° C. must not be exceeded. The following purification and isolation were effected in the case of the 1,2,3-trihydroxypropane-1,3-dicapronate-2-ethfumarate by vacuum distillation at 150° C. and 0.05 mmHg, and in the case of the 1,2,3-trihydroxypropane-1,3-dipalmitate-2-ethfumarate by recrystallization from n-hexane and acetone (MP 50.6° C.).

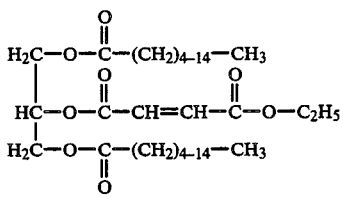

Analysis: For the empirical formula: $C_{41}H_{74}O_8$; Calculated: C 70.9, H 10.7, O 18.4; Found: C 71.0, H 10.7, O 18.6.

EXAMPLE 6

Preparation of glycerol-1,3-di-ethfumarate or 1,3-bis-ethfumaroyl-glycerol (a) 1,3-dihydroxypropan-2-one-1,3-di-ethfumarate 22.5 g (0.25 mole) of dried dihydroxyacetone were stirred into 750 ml of ethanol-free chloroform at room temperature in an $N_2$ atmosphere. 83.9 g (0.52 mole) of fumaric acid monoethylester chloride were first of all added drop by drop to the suspension and then 48.33 ml (0.52 mole) of pyridine p.a. The solution was stirred further overnight, extracted twice with water, and concentrated under reduced pressure. The residue was extracted with water and ethyl acetate. After drying with anhydrous sodium sulfate, the ethyl acetate was removed on a rotary evaporator and the residue recrystallized from methanol. There were obtained 44 g of yellow crystals of 1,3-dihydroxypropan-2-one-1,3-di-ethfumarate having a melting point of 81.4° C.

Analysis: For the empirical formula: $C_{15}H_{18}O_9$; Calculated: C 52.6, H 5.3, O 42.1, Found: C 52.6, H 5.4, O 42.1.

(b) 38 g (0.11 mole) of 1,3-dihydroxypropan-2-one-1,3-diethfumarate were dissolved in a mixture of 850 ml of tetrahydrofuran and 170 ml of benzene. The solution was cooled to 5° C. and 51 ml of water were added, drop by drop, while stirring. To this, 6.2 g (0.16 mole) of sodium boron hydride were added in separate portions, stirring being continued for an hour. Excess $NaBH_4$ was decomposed with 6 to 7 ml of glacial acetic acid and the solution allowed to stand overnight. The solution was diluted with 500 ml of chloroform and extracted with water, 1% sodium carbonate solution and water, dried with sodium sulfate and concentrated under reduced pressure. The oily residue was kept under a high vacuum for 12 hours. Yield: 28 g of clear oil.

Analysis: For the empirical formula: $C_{15}H_{20}O_9$; Calculated: C 52.3, H 5.9, O 41.8, Found: C 52.1, H 6.2, O 41.7.

EXAMPLE 7

Preparation of glycerol-1,2,3-triethfumarate and 1,2,3-tris-(ethfumaroyl)glycerol 8.77 ml (11 g; 0.12 mole) of anhydrous glycerol were dissolved in a mixture of 47.2 ml (0.4 mole) of quinoline and 500 ml of ethanol-free chloroform. 64.98 g (0.4 mole) of fumaric acid monoethylester chloride were added, drop by drop, to this solution at room temperature, followed by heating for two hours at the boiling point under reflux. The solution was diluted with 800 ml of petroleum ether and extracted with 0.5N sulfuric acid, water, 5% potassium carbonate solution and water, dried with sodium sulfate, treated for one hour with 4 g of activated carbon, suction filtered through Cellit ®, and concentrated under reduced pressure. The oily residue was kept under high vacuum for 12 hours. Yield: 27 g of clear oil.

Analysis: For the empirical formula: $C_{21}H_{26}O_{12}$; Calculated: C 53.6, H 5.6, O 40,8, Found: C 53.5, H 5.7, O 40.6.

EXAMPLE 8

Preparation of poly-1,2-propandiol-fumarate (polyester)

116.0 g (1 mole) of fumaric acid are suspended in a mixture of 99.0 g (1.3 moles) of propylene glycol, 1.0 g of hydroquinone and 5 ml of methane sulfonic acid. This mixture is heated at an internal temperature of 110° C. in a nitrogen atmosphere; thereupon, 300 ml of toluene are added. The solution is boiled under reflux for 48 hours and the water which is separated is distilled off azeotropically. A total of 35 ml of water are collected. The toluene is concentrated under reduced pressure and the oily residue is purified by washing with boiling water, 0.2N NaOH and water, and then dried for 48 hours over $P_2O_5$ in a high vacuum.

Yield: 120 g of polyester in resinous form.

EXAMPLE 9

Preparation of capsules containing 150 mg of cetyl ethyl fumarate and 80 mg of fumaric acid monoethylester calcium salt 15.0 kg of cetylethyl fumarate and 8.0 kg of fumaric acid monoethylester Ca-salt are granulated moist (NO. 800 screen) in a mixture of 21 kg of lactose, 0.5 kg. of magnesium stearate, 1.0 kg of colloidal silica (Aerosil ®) with a 2% aqueous solution of polyvinyl pyrrolidone (PVP, Collidon K30 ®) and dried. 0.5 kg FST-complex is then admixed as external phase and 460 mg per capsule of the readily flowing granulate is filled into hard-gelatine capsules of size No. 00. The granulate properties, such as particle size (determined by screen analysis), flow properties, bulk density, tamped volume and relative compacting as well as the accuracy of the dosing and uniformity of the filling material in the capsules satisfy in this connection to the requirements of the pharmacopoeias.

EXAMPLE 10

Preparation of tablets containing 165 mg of steraryl ethyl fumarate and 80 mg of fumaric acid monoethylester calcium salt 16.5 kg of ethyl stearyl fumarate and 8.0 kg of fumaric acid monethylester Ca-salt are crushed, mixed and homogenized using a No. 800 screen. A mixture of adjuvants of the following composition is prepared: 5.4 kg of microcrystalline cellulose (Avicel ®), 11.0 kg of tabletting agent T (Merck) consisting of 37.5% cellulose, 6.25% sodium carboxy methylcellulose, 18.75% colloidal silica (Aerosil 200), 6.25% magnesium stearate and 31.25% starch, as well as 5.0 kg calcium hydrogen phosphate dihydrate (CaHPO4, Emcompress ®), 3.3 kg polyvinyl pyrrolidone (Collidon CL ®). The entire powdered mixture is homogenized by means of a No. 200 screen and worked with a 2% aqueous solution of polyvinyl pyrrolidone (Collidon K 30) in the customary manner into a binder granulate and mixed in dried state with the external phase. The latter consists of 0.7 kg of a so-called FST complex containing 80% talc, 10% colloidal silica and 10% magnesium stearate.

It is then compressed in the customary manner to form tablets of a weight of 500 mg and a diameter of 10 mm, with double score.

Instead of this conventional method of tabletting, other methods can also be used for the production of tablets, such as direct tabletting, as well as solid dispersions of the pro-drugs according to the melt method and the spray dry method.

EXAMPLE 11

Production of tablets containing 237 mg of dodecyl-hydrogen fumarate and 80 mg of fumaric acid monoethylester calcium salt 23.7 kg of dodecyl hydrogen fumarate and 8.0 kg of fumaric acid monoethylester calcium salt are crushed, mixed and homogenized by means of a No. 800 screen. Thereupon the mixture of active substance is homogeneously mixed into an intimate mixture of 6.0 kg of microcrystalline cellulose (Avicel ®), 11.5 kg tabletting agent I (Merck, see Example 10), 5.0 kg of calcium hydrogen phosphate dihydrate (Emcompress ®), and 3.6 kg of polyvinyl pyrrolidone (Collidon K30), forced through a No. 200 screen and worked up with a 2% aqueous solution of polyvinyl pyrrolidone (Colloidon K30) in the customary manner to form a binder granulate to which 0.7 kg of a so-called FST complex are admixed as external phase. Compressing is effected to form tablets of a weight of 585 mg and a diameter of 12 mm, with double cross. In addition to the binder methods, other tabletting methods in accordance with Example 10 can also be used.

EXAMPLE 12

Production of an O/W emulsion ointment containing 2% of 1,3-dipalmitoyl-2-glycerol ethfumarate (full ester)

For the preparation of an easily spreadable cooling and washable O/W emulsion ointment, 2.0 kg of 1.3-dipalmitoyl-2-glycerol-ethfumarate are incorporated in a melted mixture containing 4.3 kg cetylan and 25.5 kg of hydrogenated peanut oil (Ph. Helv. VI) at 70° C. On the other hand, a solution of 2.0 kg of allantoin (5-ureidohydantoin) is dissolved in a mixture of 8.6 kg of propylene glycol, 10.0 kg of 1(+) lactic acid and 47.6 kg of water at 70° C.

The aqueous solution is incorporated in individual portions into the oily melt, and the entire mixture is emulsified and stirred cold. Shortly before solidification, it is homogenized at about 30° C. and the O/W ointment then filled into suitable tubes.

EXAMPLE 13

Preparation of a hydrogel with 3.9% octoyl hydrogen fumarate (semi-ester)

7.8 kg of monooctyl fumarate are ground with a mixture of 20.0 kg of coconut fatty acid diethanolamide (Comperlan KD ®, 50.0 kg of sodium lauryl ether sulfate Texapon N 25 ®) and 4.0 kg of urea, and a total of 100.0 kg of water at 40° C. are incorporated in individual portions into the intimate mixture.

Thereupon the pH is brought to 4.4 by means of aqueous officinal buffer solution of a pH of 5.5 of Ph.H.VI., consisting of NaOH acetic acid, and then diluted with water to a total weight of 200.0 kg. The slightly yellowish but clear, transparent hydrogel, cooled to room temperature, is filled into tubes of 10 g each. This hydrogel is suitable both as antipsoriatic douche gel and as hair shampoo.

EXAMPLE 14

Production of a brushing solution containing 6.3% dioctyl fumarate (full ester) for keratinous parts of the body (fingernails and toenails, as well as hair base)

Into 90.0 kg of a solvent mixture of 40 vol.% ethylacetate and 60 vol.% methylethyl ketone there are dissolved 6.3 kg of dioctyl fumarate and 3.3 kg of polyacrylic resin (Eudragit E 100 ®) as filmformer and 0.4 kg of dibutylphthalate as plasticizer.

This brushing solution is suitable as psoriatic agent for keratinous places of the skin, such as hair and finger and toe nails. It is optimalized with respect to adhesiveness, abrasion, removal by washing, drying properties, viscosity, spreading and adherence.

The compounds indicated below can be obtained in accordance with the examples indicated in each case, which have been described in detail above.

Compounds of general formula (I) according to Examples 1 to 4:

Propyl hydrogen fumarate, hexyl hydrogen fumarate, octyl hydrogen fumarate, dodecyl hydrogen fumarate, hexadecyl hydrogen fumarate, octadecyl hydrogen fumarate, eicosyl hydrogen fumarate, corticosteroid-21-yl hydrogen fumarate, retinyl hydrogen fumarate, glucose-6-yl hydrogen fumarate, ethyldodecyl fumarate, ethylhexadecyl fumarate, methyloctadecyl fumarate, ethyloctyl fumarate, ethylglucose-6-yl fumarate.

Compounds of general formula (II) according to Examples 5 and 6:

1,3-dipalmitoyl-2-glycerol-ethfumarate, 1,3-dipalmitoyl-2-glycerol-hydrogen fumarate, 1,3-dihexanoyl-2-glycerol-ethfumarate, 1,3-dioctadecanoyl-2-glycerol-hydrogen fumarate.

Compounds of general formula (III) according to Example 1, 2, 5 and 6:

Glycerol-1,3-diethfumarate, 2-palmitoyl-glycerol-1,3-diethfumarate, 2-palmitoyl-glycerol-1,3-bis(hydrogen fumarate), 1,3-propandiol-1,3-diethfumarate, 1,3-propandiol-1,3-bis(hydrogen fumarate), 2-hexanoyl-glycerol-1,3-diethfumarate, 2-hexanolyl-glycerol-1,3- bis(hydrogen fumarate), 1,4-butandiol-1,4-diethfumarate, 1,4-butandiol-1,4-bis(hydrogen fumarate).

Compounds of general formula (IV) according to Examples 5 and 6:

3-palmitoyl-glycerol-1,2-diethfumarate, 3-hexanoyl-glycerol-1,2-bis-(hydrogen fumarate), 2,3-diethfumaroyl-glycerol-1-phosphorylcholine, 1,2-propandiol-1,2-diethfumarate, 1,2-propandiol-1,2-bis(hydrogen fumarate), 1,2-butandiol-1,2-diethfumarate.

Compounds of general formula (V) according to Example 7:

Glycerol-1,2,3-triethfumarate, glycerol-1,2,3-bis(hydrogen fumarate), erythritol-1,2,3,4-tetrakis (hydrogen fumarate), erythritol-1,4-bis(hydrogen fumarate), 2,2-bis[(ethfumaroyloxy)methyl]-1,3-propandiol-diethfumarate.

Compounds of general formula (IX) according to Example 8:

Poly-1,2-propandiol fumarate, poly-2,3-butandiol fumarate, poly-1,2-butandiol fumarate.

Compounds which are particularly preferred in accordance with the invention are: monododecyl fumarate, monohexadecyl fumarate, monooctyl fumarate and ethylhexadecyl fumarate.

The following data will serve to provide the person having orindary skill in the art with an example for the formulation of the preparation of the invention:

Dosage data (for psoriasis):
  Oral: depending on indication, about 600 to 850 mg a day, referred to free fumaric acid.
  Topical: (Ointments and creams, hydrogels)
  Application, depending on indication, 2 to 4 times a day.

Adjuvants:
List of the adjuvants customarily used for shaping:
  Oral: (Tablets or hard gelatin capsules)
    Lactose, microcrystalline cellulose (Avicel), Na-carboxymethylcellulose, colloidal silica (Aerosil), Mg stearate, various starches, CaHPO$_4$, polyvinylpyrrolidone (PVP).
  Parenteral: The customary electrolytes, Tween 20 to Tween 80, Span 20 to Span 80, N-lauryl sulfate, PVP (Collidon), synthetic oils of low viscosity such as isopropyl palmitate or myristate, ethyl oleate, etc., Pluronic F 68, water.
  Topical: In addition to the adjuvants listed under parenterals, also 5-ureidohydantoin, hydrogenated peanut oil, cetylan, propylene glycol, glycerol, lactic acid, Comperlan KD, Texapon N 25.
  For hair and finger and toe nails: Ethyl acetate, methylethylketone, Eudragit E 100 (filmformer), dibutylphthalate (plasticizer).

Indications: Psoriasis, all forms; anti-microbial therapeutic.

Examples of formulations according to the invention:
Formulations:

| | | |
|---|---|---|
| 1. | Ethylhexadecyl fumarate | 150 mg |
| | Monoethyl fumarate Ca-salt | 80 mg |
| 2. | Monododecyl fumarate tablets | |
| | Dodecyl hydrogen fumarate | 294 mg |
| 3. | Monohexadecyl fumarate tablets | |
| | Monohexadecyl fumarate | 352 mg |
| 4. | Monooctyl fumarate film tablets | |
| | Monooctyl fumarate | 284 mg |
| | Monoethyl fumarate Zn-salt | 3 mg |
| | Monoethyl fumarate Mg-salt | 5 mg |

The treatment of three patients and the results thereof will be described below:

LR*—male—born in 1931
172 cm
82.5 kg
Illness: psoriasis
Initially: Fumadern mite ®tablets
  Dose: 3×1 tablet a day
  Duration: two weeks
  Flush; gastrointestinal disturbances
Produg: Ethylhexadecyl fumarate capsule
  Dose: 3×1 capsule a day
  Duration: 3 months
  No flush; tolerance good
  After four weeks psoriasis 75% healed
  Laboratory check-up normal AF*—female—born in 1967
152 cm
61 kg
Disease: Psoriasis
Initially: Fumadern mite ® tablets
  Dose: 2×1 tablet a day
  Duration: three months
  Flush; gastrointestinal disturbances
Produg: Monohexadecyl fumarate tablets
  Dose: 3×1 tablet a day
  Duration: four months
  No flush; tolerance good
  Psoriasis 50% healed
  Laboratory check-up normal NK*—female—born in 1934
160 cm
70 kg
Disease: Psoriasis
Initially: Fumadern mite ® tablets
  Dose: 2×1 tablet a day
  Duration: six months
  Flush; gastrointestinal disturbances
Produg: Monododecyl fumarate tablets
  Dose: 3×2 tablets a day
  Duration: four months
  No flush; tolerance good
Psoriasis 50% healed
Laboratory check-up normal

*All three patients had been suffering from psoriasis for more than seven years and before the fumaric-acid therapy they had been unsuccessfully treated topically with corticosteroid.

In view of the gastrointestinal disturbances only Fumadern mite ® (weaker dose) was tried.

Laboratory check-up: Creatinin level; blood count; transaminase and urinalysis.

What is claimed is:

1. Fumaric acid derivatives of formula (I)

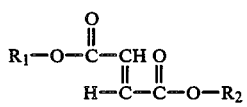

wherein
R$_1$ is ethyl or a Ca- or Zn-cation; and
R$_2$ is a saturated or unsaturated C$_6$–C$_{24}$ alkyl group.

2. A pharmaceutical composition, comprising:
  a. a fumaric acid derivative of formula (I)

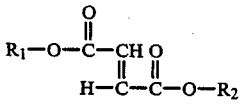

wherein $R_1$ is a hydrogen atom, a $C_1$–$C_8$ alkyl group or a metallic cation, and $R_2$ is a saturated or unsaturated aliphatic $C_6$–$C_{24}$ alkyl group in an amount which is effective for the treatment of psoriasis; and b. a pharmaceutically acceptable adjuvant.

3. The composition according to claim 2 wherein the adjuvent is selected from the group consisting of lactose, microcrystalline cellulose, Na-carboxymethylcellulose, colloidal silica, Mg stearate, starch, $CaHPO_4$ or polyvinylpyrrolidone which is suitable for shaping tablets or hard gelatin capsules for oral administration.

4. The composition according to claim 2 wherein the adjuvant is an electrolyte selected from the group consisting of Tween 20 to Tween 80, Span 20 to Span 80, N-lauryl sulfate, or polyvinylpyrrolidone, which is suitable for parenteral administration.

5. The composition according to claim 2 wherein the adjuvant is water or a synthetic oil of low viscosity selected from the group consisting of isopropyl palmitate, isopropyl myristate, ethyl oleate, or pluronic F68 which is suitable for parenteral administration.

6. The composition according to claim 2 wherein the adjuvant is selected from the group consisting of Tween 20 to Tween 80, Span 20 to Span 80, N-lauryl sulfate, polyvinyl pyrrolidone, isopropyl palmitate, isopropyl myristate, ethyl oleate, pluronic F68, 5-ureidohydantoin, hydrogenated peanut oil, cetylan, propylene glycol, glycerol, lactic acid, Comperlan KD, or Texapon N25 or water which is suitable for topical administration.

7. The composition according to claim 2 wherein the adjuvant is selected from the group consisting of ethyl acetate, methylethylketone, Eudragit E100 or dibutylphthalate which is suitable for topical administration to hair and finger and toenails.

8. A method for the treatment of psoriasis which comprises administering the pharmaceutical composition according to claim 2 in a pharmaceutically effective amount for the treatment of psoriasis to a patient in need of treatment for psoriasis.

9. A method for the treatment of psoriasis which comprises administering a compound of claim 1 in a pharmaceutically effective amount for the treatment of psoriasis to a patient in need of treatment for psoriasis.

* * * * *